United States Patent [19]

Fannin et al.

[11] Patent Number: 4,732,992
[45] Date of Patent: Mar. 22, 1988

[54] METHOD FOR RECOVERY OF ALKYLALUMINUM HALIDES

[75] Inventors: Loyd W. Fannin, Dickinson; Clark C. Crapo, Houston; Dennis B. Malpass, LaPorte, all of Tex.

[73] Assignee: Stauffer Chemical Company, Westport, Conn.

[21] Appl. No.: 944,726

[22] Filed: Dec. 22, 1986

[51] Int. Cl.⁴ .................................................. C07F 3/06
[52] U.S. Cl. ..................................... 556/129; 556/186; 556/187
[58] Field of Search .......................... 556/129, 186, 187

[56] References Cited

U.S. PATENT DOCUMENTS

| | | | |
|---|---|---|---|
| 2,996,529 | 8/1961 | Bos | 556/186 |
| 3,061,647 | 10/1962 | Jenkner | 556/129 X |
| 3,080,409 | 3/1963 | Cook et al. | 556/129 |
| 3,086,038 | 4/1963 | Gould | 556/187 X |
| 3,124,604 | 3/1964 | Hüther | 556/129 |
| 3,392,180 | 7/1968 | Hamilton | 556/129 X |
| 3,475,475 | 10/1969 | Eidt | 556/129 |
| 3,519,669 | 7/1970 | Liegler et al. | 556/129 X |
| 3,946,058 | 3/1976 | Malpass et al. | 556/186 |
| 3,969,381 | 1/1961 | Blitzer et al. | 556/129 |
| 4,092,342 | 3/1978 | Mueller | 556/186 |
| 4,118,409 | 10/1978 | Eidt et al. | 556/187 X |
| 4,670,571 | 6/1987 | Malpass et al. | 556/129 |

OTHER PUBLICATIONS

Zakharkin et al, Zhurnal Obschchei Khimii 31(11), 3662-3665 (1961).

*Primary Examiner*—Paul F. Shaver

[57] ABSTRACT

Dialkylaluminum chloride produced as a co-product in the reaction of a trialkylaluminum with zinc chloride or metallic zinc and an alkyl halide, to produce a dialkylzinc, is purified from contaminants containing zinc by contacting it with a dialkylaluminum hydride, followed by distillation.

6 Claims, No Drawings

METHOD FOR RECOVERY OF ALKYLALUMINUM HALIDES

BACKGROUND AND PRIOR ART

This invention relates to a method for the recovery of alkylaluminum halides, particularly dialkylaluminum chlorides, from mixtures which also contain zinc alkyls.

Several processes are known in the art for producing zinc alkyls, such as diethylzinc, from trialkylaluminum compounds and zinc-containing materials. One such process, described in U.S. Pat. No. 3,124,604, involves the reaction of an aluminum trialkyl with zinc chloride, producing the dialkylzinc together with co-product dialkylaluminum chloride. In another method, described in U.S. Pat. No. 3,080,409, a trialkylaluminum compound is reacted with zinc chloride in the presence of an organoaluminum halide. A third process, described in U.S. Pat. No. 3,475,475, involves the reaction of a trialkylaluminum compound with zinc and an alkyl or other organic halide.

The desired dialkylzinc product is relatively readily recovered by vacuum distillation (e.g., 47° C. at 50 torr) from the product mixture. However, the reaction co-product, dialkylaluminum halide, is contaminated with zinc-containing materials. These include higher boiling zinc alkyls such as (in the production of diethyl zinc) di-n-butyl zinc and ethyl-n-butyl zinc. These may be formed from higher boiling impurities in the trialkylaluminum or alkyl halide reactant. For instance, triethylaluminum used as a reactant may contain impurities having n-butyl groups which also react with the zinc chloride or metallic zinc to produce dialkylzincs containing n-butyl groups.

The usual method by which the desired dialkylaluminum halide coproduct (for instance, diethylaluminum chloride) is to be recovered is by distillation from the residue remaining after distillation of the dialkylzinc. However, it has been found that the higher boiling zinc alkyls tend to co-distill together with the dialkylaluminum halide so that this product, after recovery, is contaminated with substantial amounts of higher boiling zinc alkyls.

Several methods have been proposed to recover the dialkylaluminum halide co product, with relatively little zinc content. For instance, U.S. Pat. No. 3,946,058 teaches to heat the mixture strongly before such distillation in order to pyrolyze the zinc-containing compounds. However, this heating process must be carried out for a fairly long period of time (4–10 hours) at a temperature range of about 150°–240° C., which encompasses the decomposition temperature of dialkylaluminum chlorides. Additionally, zinc is formed as a product of the pyrolysis, and the zinc particles tend to clump together, producing clogging.

Another process which has been proposed for recovery of dialkylaluminum halides with a lower zinc content is described in U.S. Pat. No. 4,092,342. In this process, a dialkylaluminum chloride is treated, prior to distillation, with solid aluminum chloride. The amount of aluminum chloride utilized depends on whether or not the dialkylaluminum chloride-containing mixture also includes unreacted trialkylaluminum. This process is said to produce a diethylaluminum chloride mixture containing, in some cases less than 10 ppm zinc. However, this process still requires a heating step (at about 150° C.) prior to the addition of the aluminum chloride, and also involves the use of solid aluminum chloride, which may require additional handling.

SUMMARY OF THE INVENTION

This invention comprises an improvement in a process for production of dialkylzinc compounds by reaction of a trialkylaluminum compound either with zinc chloride or with metallic zinc and an alkyl halide, in which a dialkylaluminum halide is produced as a co-product, the dialkylzinc is removed from the reaction products by distillation, and the dialkylaluminum halide is thereafter removed from the reaction products by distillation, which improvement comprises contacting the dialkylaluminum halide, prior to removal of it by distillation, with a dialkylaluminum hydride.

DETAILED DESCRIPTION OF THE INVENTION

The material which is treated by the process of this invention consists mainly of a dialkylaluminum halide. The nature of the alkyl and halide components will depend on the process by which the primary product, dialkylzinc, was prepared (referred to as the "dialkylzinc process"). In the description of this invention, reference will be made in general to a process for production of diethyl zinc by reaction of triethylaluminum with either zinc chloride or metallic zinc and ethyl chloride. However, other dialkylzinc compounds may be produced by this process, by the reaction of trialkylaluminum compounds other than triethylaluminum and the use of alkyl halides, including iodides and bromides, other than ethyl chloride. In a preferred embodiment of this process, therefore, the dialkylaluminum halide which is to be treated for removal of zinc-containing contaminants is a lower alkylaluminum halide, preferably one containing from 1 to 4 carbon atoms in the alkyl group. More preferably this compound is a lower alkylaluminum chloride, and most preferably diethylaluminum chloride.

Also, for purposes of convenience, the improvement which comprises this invention will be referred to specifically in terms of treatment with diethylaluminum hydride (DEAH), but the process may be carried out using other dialkylaluminum hydrides in which the alkyl groups contain from 1 to 8 carbon atoms.

In the dialkylzinc process, a dialkylzinc compound such as diethylzinc is produced by reaction of the corresponding trialkylaluminum compound (in this case triethylaluminum) either with zinc chloride or with metallic zinc and the corresponding alkyl halide (in this case ethyl chloride).

The reaction of triethylaluminum with zinc chloride is described in U.S. Pat. No. 3,124,604 and is carried out without a catalyst. See, for instance, Example I of this U.S. patent.

The production of diethyl zinc by reaction of metallic zinc (i.e., zinc dust), triethylaluminum and ethyl chloride is described in U.S. Pat. No. 3,475,475. This process may be enhanced by the inclusion of elemental iodine as a catalyst.

Whichever process is used, the reaction product comprises primarily two components: the desired zinc alkyl, i.e., diethylzinc and a dialkylaluminum halide, i.e., diethylaluminum chloride. In the reaction between zinc chloride and triethylaluminum, the diethylaluminum chloride is produced in twice the molar amount of diethylzinc, because of reaction stoichiometry.

As is known in the prior art, the diethylzinc product is readily removed from the total reaction products by appropriate distillation, for instance, vacuum distillation. The major component of the remaining product is thus diethylaluminum chloride, which will contain various amounts and types of zinc impurities, such as unreacted zinc chloride, minor amounts of undistilled diethylzinc, and volatile zinc alkyls having higher boiling points than that of diethylzinc. Such zinc alkyls would include, for instance, di-n-butylzinc and n-butylethylzinc, which are believed to be produced in the dialkylzinc process by reaction of zinc chloride with n-butyl-containing contaminants in either the triethylaluminum or ethyl chloride. When, as conventionally, the co-product diethylaluminum chloride is recovered by distillation, these volatile zinc alkyl impurities generally tend to distill off with the diethylaluminum chloride and contaminate this product.

According to this invention, the addition of diethylaluminum hydride (DEAH) or another dialkylaluminum hydride to the diethylaluminum chloride product after distillation of diethylzinc has been completed but before distillation of diethylaluminum chloride is carried out, enables the recovery of a mixture of ethylaluminum chlorides containing relatively low amounts of zinc contaminants.

According to the prior art, specifically U.S. Pat. No. 3,124,604 (col. 3, lines 12-22) the presence of a dialkylaluminum hydride in a process of this type is generally considered undesirable as it causes the formation of metallic zinc, coloring the reaction products and making it more difficult to work them up. Thus, that reference recommends the use of a trialkylaluminum (such as triethylaluminum) which is free from dialkylaluminum hydrides.

According to our invention, on the other hand, the use of dialkylaluminum hydrides is beneficial at this later stage of the process in removing zinc containing contaminants, particularly the volatile zinc alkyls, from the final reaction products, making it possible to more readily obtain the desired co-product dialkylaluminum halide.

The amount of dialkylaluminum hydride employed will depend on the amount of soluble zinc in the liquid mixture. Subsequent to the distillation of diethyl or other dialkylzinc, the zinc content of the remaining liquid is determined (after first separating off any solids) by suitable analytical techniques. The zinc contained in the liquid (that is, prior to the distillation of the dialkylaluminum hydride) is referred to as "soluble zinc". The amount of dialkylaluminum hydride employed will be from about 1 to about 20% by weight, with respect to the weight of the soluble zinc. Most preferably, the weight ratio is from about 2 to about 20%. The step of contacting the dialkylaluminum halide with dialkylaluminum hydride is generally conducted at ambient temperatures and atmospheric pressure. The temperature may be as high as about 150° C.

The dialkylaluminum hydride may be introduced as such, but preferably, especially in the case of relatively lower boiling hydrides, it is introduced as a mixture with the starting material trialkylaluminum. In such mixtures, the dialkylaluminum hydride is most preferably contained as a relatively minor component, for instance in an amount of from about 1 to about 10% by weight in the trialkylaluminum. This would correspond to about 0.1 to about 1.0 weight percent equivalent aluminum hydride. Preferably, the alkyl groups of the dialkylaluminum hydride are identical with those of the dialkylaluminum halide and trialkylaluminum so as to prevent contamination with additional alkyl components.

Alternatively, a higher boiling dialkylaluminum hydride such as di-(n-octyl)aluminum hydride may be introduced per se in relatively small amounts. Again, in an amount of from about 1 to about 20, preferably from about 2 to about 20% by weight, with respect to the weight of soluble zinc contaminant. The higher boiling dialkylaluminum hydride will remain in the still pot and not contaminate the dialkylaluminum halide product. It is also possible to introduce a lower alkyl dialkylaluminum hydride such as diethylaluminum per se, but since only a small amount is desired for the removal of zinc contaminants, it may be difficult to excercise fine control over the amount of the diethylaluminum hydride introduced, which could result in contamination of the product halide with diethylaluminum hydride.

The distillation and recovery of diethylaluminum chloride from the contaminated material is carried out according to known techniques. The material, after distillation and recovery, according to this invention, contains generally less than about 600 ppm zinc, and in most cases substantially less than that amount.

The conduct of the process according to this invention is illustrated in greater detail in the example which follows.

EXAMPLE

Diethylzinc was prepared by the slow addition of one molar equivalent of anhydrous zinc chloride powder to two molar equivalents of triethylaluminum followed by heating to about 75° C. for one hour. The reaction product contained basically two molar equivalents of diethylaluminum chloride and one molar equivalent of diethylzinc.

Diethylzinc was distilled off from the reaction product by vacuum distillation at about 48° C. under 50±2 torr pressure, with the pot temperature not exceeding 135° C.

Prior to the distillation of the diethylaluminum chloride, the mixture remaining after diethylzinc distillation was divided into two portions. To one portion (total 89 g) there was added 12.1 g of triethylaluminum containing 2.93 weight percent diethylaluminum hydride (equivalent to 0.35 weight percent aluminum hydride). The other portion of the bottoms were not treated with hydride.

Each of the bottoms material comprising primarily diethylaluminum chloride, including the solids, was charged to a column for distillation. Then, diethylaluminum chloride was removed from each of the remaining materials by vacuum distillation at about 88° C. under a pressure of 10±2 torr. The diethylaluminum chloride was removed in two fractions. The distillate was found to contain 100 ppm zinc by atomic absorption analysis. Similar analysis of the untreated portion of the bottoms showed 189 ppm zinc in the distillate.

What is claimed is:

1. In a process for the production of dialkylzinc compounds by reaction of a trialkylaluminum compound either with zinc chloride or with metallic zinc and an alkyl halide, in which a dialkylaluminum halide is produced as a co-product, the dialkylzinc is removed from the reaction products by distillation, and the dialkylaluminum halide is thereafter removed from the reaction products by distillation, the improvement comprising contacting the dialkylaluminum halide, prior to removal of it by distillation, with a dialkylaluminum hydride.

2. A process according to claim 1 in which the dialkylaluminum hydride has from 1 to 8 carbon atoms in the alkyl groups.

3. A process according to claim 1 in which the dialkyl zinc compound is diethyl zinc, the trialkylaluminum compound is triethylaluminum, the dialkylaluminum chloride is diethylaluminum chloride, and the dialkylaluminum hydride is diethylaluminum hydride.

4. A process according to claim 1 in which the dialkylaluminum hydride is introduced as a mixture with trialkylaluminum compound.

5. A process according to claim 4 in which the dialkylaluminum hydride is present in an amount of from about 1 to about 10 weight percent, based on the trialkylaluminum compound.

6. A process according to claim 1 in which the amount of dialkylaluminum hydride added is from about 1 to about 20% by weight with respect to the weight of soluble zinc contaminant.

* * * * *

UNITED STATES PATENT AND TRADEMARK OFFICE
CERTIFICATE OF CORRECTION

PATENT NO. : 4,732,992

DATED : March 22, 1988

INVENTOR(S) : Loyd W. Fannin et al.

It is certified that error appears in the above-identified patent and that said Letters Patent is hereby corrected as shown below:

On the title page assignee should read -- Texas Alkyls, Inc., Deer Park, Texas-

Signed and Sealed this

Fifth Day of July, 1988

Attest:

DONALD J. QUIGG

*Attesting Officer*   *Commissioner of Patents and Trademarks*